United States Patent
Shah et al.

(10) Patent No.: US 8,632,963 B2
(45) Date of Patent: Jan. 21, 2014

(54) METHOD FOR IMPROVING CELL PERMEABILITY TO FOREIGN PARTICLES

(75) Inventors: Jyotsna Shah, Santa Clara, CA (US); Helena Weltman, Los Altos, CA (US)

(73) Assignee: ID-FISH Technology Inc., Santa Clara, CA (US)

( * ) Notice: Subject to any disclaimer, the term of this patent is extended or adjusted under 35 U.S.C. 154(b) by 1630 days.

(21) Appl. No.: 11/494,430

(22) Filed: Jul. 27, 2006

(65) Prior Publication Data

US 2007/0042358 A1 Feb. 22, 2007

Related U.S. Application Data

(60) Provisional application No. 60/703,329, filed on Jul. 28, 2005.

(51) Int. Cl.
*A01N 47/00* (2006.01)
*B01D 19/00* (2006.01)
*C12Q 1/00* (2006.01)
*C12M 1/33* (2006.01)
*C12M 1/00* (2006.01)
*C07H 21/02* (2006.01)

(52) U.S. Cl.
USPC ............... 435/4; 435/6.1; 435/306.1; 435/5; 435/6.12; 435/307.1; 252/188.2; 514/515

(58) Field of Classification Search
None
See application file for complete search history.

(56) References Cited

U.S. PATENT DOCUMENTS

| | | | |
|---|---|---|---|
| 5,422,277 A | 6/1995 | Connelly | |
| 5,521,300 A | 5/1996 | Shah | |
| 5,597,688 A | 1/1997 | Connelly | |
| 5,629,156 A | 5/1997 | Shah | |
| 6,165,723 A | 12/2000 | Shah et al. | |
| 6,538,107 B1 * | 3/2003 | Hinuma et al. | 530/350 |
| 6,835,393 B2 | 12/2004 | Hoffman | |
| 7,307,103 B2 * | 12/2007 | Prusiner et al. | 514/557 |
| 2005/0059054 A1 | 3/2005 | Conrad et al. | |
| 2005/0136102 A1 | 6/2005 | Hoffman et al. | |

OTHER PUBLICATIONS

Carlisle, et al., "Nicotine signals through muscle-type and neuronal nicotinic acetylcholine receptors in both human bronchial epithelial cells and airway fibroblasts" Respriratory Research, vol. 5, No. 27, Dec. 10, 2004, pp. 1-16.

* cited by examiner

*Primary Examiner* — Catherine Hibbert
(74) *Attorney, Agent, or Firm* — Pierce Atwood LLP; Kevin M. Farrell; David J. Wilson

(57) ABSTRACT

The present invention provides a method for allowing foreign particles to penetrate, very efficiently, the cell wall, cell membrane, organelle membrane and/or nuclear membrane of a cell and hybridizing or binding to the complimentary target in the cell. The cells may be from a culture or from specimens obtained from a patient. The foreign particle can be a probe consisting of, for example, either individually or in any combination of two or more of the following: DNA, RNA, peptide nucleic acids (PNA), glycopeptides, lipopeptides, glycolipids or prions. The target is a cell, a cell component or, preferably, a pathogen or pathogen component. The pathogen can be, for example, bacteria, fungi, yeast or viruses.

12 Claims, No Drawings

SEQUENCE LISTING

<160> NUMBER OF SEQ ID NOS: 5

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
agaacacgcc actattcaca cgcgcgtatg c                                    31

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
ttcgaggtta gatgccc                                                    17

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
atcgcccgca cgctcacagt taagccgtga gatttc                               36

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
gcattacccg ctggc                                                      15

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cttggctcta atacagtcgg                                                 20

METHOD FOR IMPROVING CELL PERMEABILITY TO FOREIGN PARTICLES

FIELD OF THE INVENTION

The present invention relates to compositions and methods for improving cell permeability to foreign particles including the probes of the present invention.

BACKGROUND

Cells are the basic unit of all living organisms. The one common attribute of almost all cells is that they are surrounded (or bounded) by a cytoplasmic membrane. This membrane harbors the internal contents of the cell and regulates the movement of substances into and out of the cell. Only those molecules that can diffuse across the membrane or are transported across it can move into and out of the cell. Some can pass through the lipid core of the membrane, but others must pass through pores. Still other molecules must cross the membrane attached to carriers in an energy dependent manner. Likewise, the nucleus and other cellular organelles have membranes to regulate the flow of molecules into and out of the organelle.

Fixation is a chemical process that "sets" cellular molecules in place so that the cell or tissue can then be studied. Most agents that are used as fixatives (e.g., alcohols such as ethanol and aldehydes such as paraformaldehyde) work by crosslinking cellular molecules, especially proteins. This crosslinking process prevents the degradation of the cellular structure. Various fixatives are better suited for the preservation of different cellular molecules and structures or for different detection methods. The fixative chosen for any particular purpose will be determined by the nature of that purpose.

Unfortunately, the current methods of fixation often hamper the subsequent ability of a researcher or clinician to detect internal cellular components. In other words, the very thing that prevents the degradation of the cell, fixation, can also set up a barrier to the many types of research and diagnosis that rely on larger sized detection molecules. Because of this, efforts have been made to permeabilize cells or make channels after fixation.

Current methods of permeabilizing the cell membrane after fixation are not effective for all specimens, are too rigorous (thus, destroying the structures to be studied) and/or require expensive equipment. For example, Hoffman, et al. (U.S. Pat. No. 6,835,393) disclose the use of polycarboxylic acid polymers and pH for disrupting cell membranes only for use in non-fixed samples. Connelly, et al., (U.S. Pat. Nos. 5,597,688 and 5,422,277) disclose the use of a composition with 2,4-dinitrobenzene sulfonic acid, 2,4-dinitrobenzoic acid or 2,4-dinitrophenol for both cell membrane fixation and permeabilization but these compositions limit the researcher's or clinician's choice of fixative and, thus, limits necessary assay flexibility. Mechanical methods such as sonication, electroporation, etc. usually only work on unfixed samples and require expensive equipment.

Furthermore, the available research and diagnostic methods of the prior art for many cellular targets such as pathologies depends on microscopic evaluations, cellular morphological parameters, staining characteristics and the presence or absence of certain targets. However, many of these diagnostic methods are not entirely accurate or sufficiently sensitive.

What is needed are compositions and methods for the improved permeability of cell membranes of specimens to foreign particles such as labeled detection molecules. Furthermore, what is needed are compositions and methods for the improved detection of cellular targets and pathogens.

SUMMARY OF THE INVENTION

In one embodiment, the invention allows detection of the target or target fragment, directly from cells in a cell culture or specimen obtained from a patient, by in situ hybridization. In a preferred embodiment, the cell is a pathogen. The method is comprised of several steps that are performed, preferably, but not necessarily, in the listed order. A sample of the culture or specimen is deposited onto a slide. The sample is fixed onto the slide either by heat or with a standard fixative. The fixative can be, for example, methanol, methanol acetic acid, acetone, formaldehyde or formalin. The fixed sample is treated with the IDF solutions (see, Infra), stained or probed and observed. Alternatively, the specimen is mixed with IDF solution, incubated, then smeared or otherwise placed onto a glass slide, air-dried and fixed. The IDF solution can comprise of any combination of the following reagents: chaotropic salts (e.g., guanidine thiosulphate or hydrochloride), ionic detergents (e.g., SDS) and/or non-ionic detergents (e.g., IPGEL, deoxycholate, cholate or bile salts) or other reagents with similar properties, methanol and acetic acid. The concentration of each reagent in the IDF solution depends, for example, on the cell wall of the pathogen to be detected. Although the present invention is not limited by any theory or mechanism, it is believed that the IDF solution makes "channels" in the cell wall and/or membranes (cellular and nuclear) of the pathogen. These channels allow a probe to penetrate the cell wall and cell membrane and enter the cytoplasm and/or the nucleus of the pathogen. The probe of the present invention may comprise DNA, RNA, PNA, peptide, glycopeptide, lipoprotein, or glycolipid or a mixture of any of the above. The targets of the fixed cells in the sample are contacted with a probe complex (the probe complex comprises binding agents specific for the target) specific for the target under conditions appropriate for hybridization or binding (for example: as described in U.S. Pat. No. 6,165,723 to Shah and Harris, which is incorporated herein by reference). Non-hybridized or non-bound probe may then be rinsed from the sample. In one embodiment, the rinsed sample may then be stained with an appropriate counterstain (e.g., Evans Blue, DAPI, potassium permanganate, etc). The hybridized or bound probe complex is visually detected by, for example, microscopy, with the presence of the probe complex being an indication of the presence of the cell target. The method can be performed with different hybridization buffers, several non-limiting examples of which are disclosed herein and in U.S. Pat. No. 6,165,723 to Shah and Harris, which is incorporated herein by reference). The hybridization buffer used is determined by the nature of the probe used. The method of the present invention is useful for detecting cells, cell constituents and, preferably, pathogens in a specimen. Exemplary, non-limiting specific probe complexes are disclosed herein that are useful for detecting pathogens of the species *Mycobacteria*.

The methods of the present invention are useful, for example, in detecting nucleic acids, peptides, glycopeptides, lipopeptides and glycolipids from a wide variety of specimens. Exemplary specimens include, for example, cells, cell types, tissues or a pathogen or pathogens of interest including or derived from, e.g., serum, plasma, sputum, urine, cerebral spinal fluids, tissues and breast milk. The compositions and methods of the present invention may be used on specimens from any organism including, but not limited to, mammals, reptiles, fish, birds, plants and insects.

In one embodiment, the present invention contemplates a composition (IDF solution) for increasing the permeability of cell walls, cell membranes, organelle membranes and nuclear membranes, said composition comprising in one embodiment: GuSCN (guanidine thiocyanate), Tris-HCL, EDTA, IGEPAL (octylphenoxy poly(ethyleneoxy)ethanol), acetic acid, methanol, sodium cholate and sodium deoxycholate. The present invention further contemplates that the GuSCN is at a concentration of approximately 2.0 to 3.3M; the Tris-HCL is at a concentration of approximately 10 to 100 mM; the Tris-HCL is at a pH of approximately 7.0 to 9.0; the EDTA is at a concentration of approximately 5 to 50 mM; the IGEPAL is at a concentration of approximately 0.1 to 2.0 percent; the acetic acid is at a concentration of approximately 0.1 to 10.0 percent; the methanol is at a concentration of approximately 20 to 50 percent; the sodium cholate is at a concentration of approximately 0.02 to 2.5 percent and the sodium deoxycholate is at a concentration of approximately 0.02 to 2.5 percent.

In another embodiment GuSCN buffer is replaced with GuHCL buffer between about 2M to 6M. In still another embodiment IGEPAL is replaced with SDS between about 0.01% to 2.0%. In yet still another embodiment GuSCN is used in conjunction with GuHCL and/or IGEPAL is used in conjunction with SDS.

In one embodiment, the present invention contemplates a method for staining a target in a cell, comprising: a) contacting the cell with a composition comprising GuSCN (guanidine thiocyanate), Tris-HCL, EDTA, IGEPAL (octylphenoxy poly(ethyleneoxy)ethanol), acetic acid, methanol and sodium deoxycholate to create a permeabilized cell; b) contacting the permeabilized cell of step (a) with a binding agent specific for binding to said target, and; c) detecting said binding agent of step (b).

In other aspects, the invention contemplates that the target of the above method is selected from, for example, nucleic acids, peptide nucleic acids, peptides, glycoproteins, lipids, lipoproteins, viruses, prions and mycoplasma.

In other embodiments, the present invention contemplates that the binding agent is selected from a group consisting of nucleic acids, peptide nucleic acids, peptides, lipoproteins, glycoproteins, antibodies or antibody fragments and lipids.

The binding agent of the present invention may additionally comprise a detection moiety and the detection moiety may be selected from a group comprising, for example, fluorescent markers, radioactive markers, dyes, colloidal metals, biotin/avidin, horseradish peroxidase, etc. In a preferred embodiment, the detection is via a labeled antibody with affinity for the target antigen. A binding agent comprising a detection moiety is defined herein as a probe complex.

In one embodiment a clinical sample is treated with IDF solution in the tube, followed by boiling to release nucleic acid in solution. This technique is effective for targets such as *Mycobacteria*, fungi and yeasts that require mechanical lysis (e.g. by sonication) or long incubations with enzymes to digest the cell walls, for example. The target of interest can be further purified by (1) standard DNA purification techniques or (2) by sandwich hybridization using specific probes. The purified target DNA and RNA can then be amplified by PCR or RT-PCR respectively, if necessary, prior to detection.

In a more preferred embodiment, the target is a nucleic acid from the microorganism *Mycobacterium tuberculosis* and the binding agent is an oligonucleotide (or PNA probe) complementary to nucleic acids from the microorganism *Mycobacterium tuberculosis*.

In another aspect, the method also comprises background staining to better highlight or visualize the detection moiety. Background stains and staining techniques are known to those practiced in the art.

DETAILED DESCRIPTION OF THE INVENTION

The present invention is based on the discovery of an improved method of allowing the probe to penetrate the cell wall and/or cell membrane of a cell (e.g., a pathogen) for directly detecting the presence of a target nucleic acid, protein, peptide, lipopeptide, glycopeptide, lipid, etc., in cells from culture or from specimens obtained from an individual (e.g., blood smears, biopsies, paraffin embedded tissues and ticks), by in situ hybridization. The invented method is particularly well suited for detecting nucleotide sequences specific to pathogens that which are found within, for example, sputum, whole blood, central spinal fluid (CSF), other body fluids or infected tissues. More specifically, novel improvements of the traditional fixation/pretreatment methods are described that allow probes (e.g., oligonucleotide probes) to penetrate inside cells (e.g., pathogens such as bacteria, viruses, fungi, yeast and protozoans), which may be located either inside or outside infected host cells. In addition, a procedure with a counterstain (e.g., DAPI, Evans Blue, potassium permanganate) after hybridization with fluorescence labeled probe allows the organisms that retain the hybridized probes to be easily visualized in culture or clinical samples.

The novel and unique in situ hybridization pretreatment procedures, detection techniques and compositions of the present invention described herein allow the use of recombinant DNA, RNA, PNA, peptide, glycoproteins, lipids and glycolipid probes in cells, microorganisms or tissue sections and is compatible with microscopic examination routinely performed in bacteriology, parasitology, histology or pathology laboratories. The present invention applies, for example, a nucleic acid probe of predetermined nucleotide sequence to the sample cells (or tissue) and to the examination of the sample by, for example, microscopy, electron microscopy, flow cytometry or radioactive imaging (e.g., X-ray film, phosphorimaging), to determine which cells (or tissues) within the population contain the specific targets (e.g., nucleic acid sequences) of interest. Thus, in infected whole blood smears or tissue sections, pathogenic organisms such as bacteria, virus, protozoan or fungi can be detected within the infected cells. Such protocols provide useful diagnostic and scientific information since the presence or absence of a specific nucleic acid can correlate with one or more cells of observable structure and morphology, and, in this way, provide a basis for clinical diagnosis and prognosis.

The method for detecting a target nucleic acid fragment directly from a specimen is comprised of steps that are to be performed, preferably, in the order(s) listed. A specimen, usually obtained from an individual, is first deposited onto a slide. The sample is fixed onto the slide with fixative (e.g., methanol, methanol-acetic acid fixative or a formalin-acetic acid fixative). Once the sample is fixed, the sample cells are permeabilized with the compositions and methods of the present invention. Alternatively, the specimen is mixed with IDF solution in a tube, incubated and then deposited onto a slide, air dried and fixed. Next, the cells are contacted with a probe specific for the target under conditions appropriate for hybridization.

After an adequate period of hybridization any non-hybridized probe is rinsed from the sample. In a preferred embodiment, the sample is then contacted with a counterstain (e.g., DAPI, Evans Blue, Potassium permanganate, etc.). Regardless if the sample was counterstained, probes that are hybridized to the target of the sample are then visually detected by, for example, microscopy. The presence of probe within the sample is an indication of the presence of the target fragment. Counterstaining the sample concurrently or sequentially with the in situ hybridization assay of the present invention enhances the method by allowing, for example, a clearer determination of the location of the target within the sample. Such information helps, for example, to provide a clearer determination of background hybridization.

This method is suitable for use with any specimen obtained from an individual. This includes, without limitation, whole blood, serum, plasma, sputum, urine, breast milk, cerebral spinal fluid and tissue. This method is also suitable for detection of a pathogen or other target within the cells of an insect vector, insect cell, plant cells, fungi and bacteria.

The purpose of fixing cells or tissue is to immobilize the cells and to preserve the morphology of the cells or tissue so cell constituents such as, for example, RNA are retained within the cellular matrix during in situ hybridization. The preferred method thus utilizes a fixative which is able to preserve and retain nucleic acids of the cell and at the same time cross-link and/or precipitate the proteins in the cellular matrix such that the cell or tissue remains substantially in open configuration for probe penetration and subsequent hybridization.

In a preferred embodiment, the probes of the present invention comprise, for example, synthetic or biologically produced nucleic acids (DNA, RNA and equivalents); peptide nucleic acids (PNA; and equivalents); peptides (and equivalents) that contain specific nucleic acid or peptide sequences which hybridize under stringent conditions to specific cellular targets. In another embodiment, the probes of the present invention comprise synthetic or biologically produced glycopeptides, lipopeptides and prions or prion-like molecules (or the equivalents thereof) that bind under stringent conditions to specific targets within the cell.

The probe complex is defined as a probe that comprises a marker moiety suitable for detection. If the probe is a nucleic acid, the marker moiety is attached at either the 5' end, the 3' end, internally, or in any combination thereof. The preferred marker moiety is an identifying label such as radiolabel (e.g., $P^{32}$, $I^{125}$, $H^3$), a biotin label or a fluorescent label. Alternatively, the probe has a labeled poly-deoxynucleotide tail that is used for detection of the probe complex. The probe complex may also be comprised of a plurality of different nucleic acid sequences, PNA, peptides, glycopeptides, lipopeptides or prions or any combination thereof comprising one or more labeled with a marker moiety. If more than one of the probe moieties are labeled it may be beneficial to label the each of the probe moieties with a different marker moiety.

The nucleotide sequence of an oligonucleotide probe is substantially complementary to at least a portion of the target nucleic acid. The target nucleic acid is either a nucleic acid normally present within the fixed cell or tissue or, alternatively, that is not normally present in the cell or tissue and is associated with an abnormal or pathological state. Each probe complex molecule is preferably comprised of a DNA or RNA fragment ranging in size from about 10-50 nucleotides.

Peptide probes include, for example, antibodies and other molecules known of binding a defined target or range of targets. Examples of non-antibody probes included, for example, enzymes and enzyme substrates and the effecter portions thereof. Additionally, known drugs or chemicals may selectively bind target proteins (e.g., antibiotics may bind bacteria). Lipopeptides, for example, are useful for the detection of lipid moieties in a cell including specific organelles or portions of organelles and bacteria internalized in a cell. Glycopeptides, for example, interfere with platelet aggregation and, therefore, may be used to target molecules necessary in platelet function thereby aiding in research and diagnosis of clotting abnormalities. Prions, or portions thereof may be used, for example, as probes for neurological tissues. Likewise, prions may be targets in fixed samples.

In a preferred embodiment, the probe is added to the sample in excess of the target (e.g., 10:1, 100:1 or 1000:1). This is to drive the hybridization reaction efficiently and to promote a high rate of probe:target binding.

The probe complex (comprising, for example, DNA, RNA and or PNA) is contacted with the target of the sample (e.g., nucleic acids) of the fixed sample, generally by adding a solution of probe complex onto the sample. Exemplary conditions appropriate for hybridization are solutions that provide the appropriate buffered environment. Some examples of appropriate hybridization buffers are:
1) a buffer comprising between about 10% and 50% formamide, 2×.SSC (pH 7.4), and 1% NP40;
2) a buffer comprising between about 1.5 M and 4 M GuSCN buffer;
    5 M GuSCN stock buffer is made from 5 M GuSCN, 100 mM Tris-HCl (pH 7.8), 40 mM EDTA, 1% NP40. This stock buffer is diluted to the indicted molarity of GuSCN by the addition of 1×TE pH 7.8 to produce the above referenced GuSCN buffer molarities.
3) a buffer comprising between about 2 to 6 M GuHCl buffer.
    8 M GuHCl stock buffer is made from 8 M GuHCl, 200 mM Tris-HCl, (pH 7.8), 40 mM EDTA, 1% NP40. This stock buffer is diluted to the indicated molarity of GuHCl by the addition of 1×TE pH 7.8 to produce the above referenced GuHCl buffer molarities.
4) a buffer comprising of a mixture of formamide (20-50%) and GuSCN buffer. (e.g. 0.5M to 3M)
5) a buffer comprising of a mixture of GuSCN buffer. (e.g. 0.5M to 3M) and GuHCL buffer (e.g. 1M to 5M)

The specific composition and concentration of hybridization buffer varies with the type of probe or probe complex used. The composition and concentration of buffer used is, also, dependent on the Tm (melting point: the temperature at which double stranded DNA separates forming two complementary single strands) of the probe, probe sequence, probe length and hybridization temperature and can be determined by one of skill in the art through the course of no more than routine experimentation.

The present invention is not limited to any particular hybridization temperature. However, it should be appreciated that the use of formamide in the hybridization buffer allows hybridization to be carried out at a much lower temperature than standard hybridization protocols. For example, hybridization of an average probe complex specifically to the target (and not to host cells) in aqueous hybridization buffer such as sodium chloride would generally require a temperature of about 60-65° C. The same hybridization performed at about 42° C. in hybridization fluid 1) above, would provide equivalent specificity.

Likewise, the use of GuSCN also allows hybridization to be carried out at a much lower temperature than standard hybridization protocols. For example, in an average procedure, hybridization of the probe specifically to the target (and not to host cells) in aqueous hybridization buffer such as sodium chloride would require temperatures of approximately 60-65° C. However, the same hybridization performed in the GuSCN or GuHCl hybridization buffer above, at about 37° C. will provide equivalent specificity of hybridization.

After hybridization is complete, the non-hybridized probe is rinsed from the sample, generally by applying a series of washes with a wash buffer. It is within the means of those skilled in the art to determine appropriate wash buffers and wash times. In one embodiment, the wash buffer comprises 0.3 M sodium chloride, 0.03 M sodium citrate, and 0.1% SDS. Another appropriate wash buffer comprises phosphate buffered saline (PBS).

After rinsing, the sample may be counterstained. In one embodiment, counterstaining of the background enhances the visualization of the hybridized probes. Preferred counterstains are, for example, DAPI, Evans Blue and potassium permanganate. Other appropriate counterstains are known by those practiced in the art. This staining step is generally applied when a fluorescent-labeled probe is used to detect nucleic acids, proteins, glycoproteins and lipoproteins that are specific for a target. Although helpful, the counterstains are not required for the embodiments of the present invention.

The probe is detected by means suitable for the specific moiety used to label the probe complex. The preferred method for detecting fluorescent-labeled probes, for example, employs special green, red and blue microscope filters (i.e., fluorescent microscopy). Hybridized radiolabeled probes can be detected by, for example, autoradiography and phosphorimaging. Biotin labeled probes can be detected by enzymatic detection systems and such detection systems are commercially available.

The method described above allows for the simultaneous detection of different pathogens in a single clinical sample by performing one reaction with a probe complex that is comprised of a plurality of different nucleic acid sequences, each labeled with a different marker moiety. For simultaneous detection the different oligonucleotide probes, which are specific for the different nucleic acids of the different targets commonly present in the specimen, they can be designed such that the Tm (melting point) values of all the probe complex sequences are very similar. Each specific oligonucleotide is then labeled with a different detectable moiety (e.g., different fluorescent moieties). Hybridization is performed with the multiple components of the probe complex. The hybridized sample is processed as described above and the sample is observed by means appropriate for detection of the different labeled oligonucleotides of the probe complex (e.g., viewed using appropriate filters if different fluorescent moieties are used) to detect which of the targets is present in the sample.

It will be recognized by practitioners ordinarily skilled in this art that the novel pretreatment protocol for use with the in situ hybridization protocol described herein is compatible with all previously known methods of detection as well as the ones described herein and is not limited by the method of detection used. The in situ hybridization protocol has been streamlined so that fewer manipulations are necessary and can therefore be performed in a short time. Embodiments of the present invention also encompass kits comprising the compositions of the present invention. Such compositions when provided in a kit form will allow the practice of various embodiments of the protocols presented herein including those that have been optimized for simplicity and for compatibility with a wide variety of detection methods. It is also expected that such prepared kits containing specifically prepared reagents and probes will be applicable in clinical/diagnostic laboratories, where the ability to detect the presence or absence of specific nucleic acids would serve to positively or negatively identify pathological states characterized by the presence of specific targets.

The available diagnostic methods of the prior art for many cellular pathologies depends on microscopic evaluations, cellular morphological parameters, staining characteristics, and the presence or absence of certain targets. However, many of these diagnostic methods are not entirely accurate or sufficiently sensitive. In situ hybridization using the above described protocol and pathogen specific probes will allow easier and more accurate identification of targets (including, but not limited to, pathogens) in samples.

The present invention provides a simple pretreatment protocol for use in in situ hybridization protocols that provides enhanced probe penetration into cells and, thus, improves hybridization and detection characteristics as compared to previously described protocols. The improvements include maximizing the sensitivity of the assay by increasing efficiency of hybridization and detection of specific "signal." Although the present invention is not limited to any particular mechanism, it is believed that the increased sensitivity is due to improved hybridization due to improved probe penetration into the cells and, at the same time, maximized retention of the target (e.g., nucleic acid sequences) in the cell or tissue and, maximizing preservation of the other biochemical and morphological characteristics of the cell or tissue sample.

EXPERIMENTAL

A preferred and non-limiting use of the above method is in the detection of *Mycobacterium tuberculosis* from a culture or from sputum. It will be understood and appreciated by one of skill in the art that the novel methodology is equally applicable to a wide variety of other systems, cells, tissue cultures and tissues for hybridization of specific nucleic acids (or detection of other cellular components of the target cells, tissues or pathogens) of interest with concomitant preservation of cell integrity and morphology.

EXAMPLE

The culture or patient's processed sputum was smeared onto a glass plate and air-dried. The cultured cells were washed and concentrated by centrifugation. The washed cells were suspended in phosphate buffer with BSA. To render the cells inactive the suspended cells were boiled for 15 minutes at 100° C.

Sample Preparation Method 1

Sputum was be processed by either 1) NALC/NaOH or 2) NALC/NaOH followed by boiling the processed sputum for 15 minutes at 100° C. to render the sample inactive or 3) with a chaotropic solution such as guanidine hydrochloride or thiosulphate (briefly, 2-3 volumes of 5M GuSCN or 8M GuHCL to sputum were mixed). The sample was incubated at 37° C. for 20 minutes. The sample was centrifuged to pellet the cells. The cells were washed with phosphate buffered saline. Washed cells were suspended in phosphate buffered saline with 1% BSA or 4) a chaotropic solution such as guanidine hydrochloride or thiosulphate followed by boiling (same as step 3, above) except the suspended cells in buffered saline with 1% BSA are boiled for 15 minutes at 100° C. to kill *Mycobacteria*. The prepared culture or sputum sample was then smeared onto a glass slide and air-dried.

The sample was fixed by methanol or methanol-acetic acid or ethanol. The fixed smear was treated with the IDF solution (as disclosed Supra) for 10 minutes. After 10 minutes the smear was washed 3 times with PBS and air-dried.

Sample Preparation Method 2

One volume of a patient's unprocessed sputum was mixed with two volumes of IDF solution (Supra) in a tube and incubated at room temperature (20-25° C.) for 15 minutes. The sputum-IDF mixture was then smeared onto a glass slide, air dried and fixed with methanol. The IDF treatment of the fixed smear prior to hybridization was omitted. Before hybridization the slide was washed with PBS three times.

Sample Preparation Method 3

The methanol fixed sputum-IDF mixture on a glass slide was treated with 2% glutaraldehyde in PBS for 5 minutes at '20-25° C. (ambient temperature), then rinsed with PBS three times and air dried. The IDF treatment of the fixed smear prior to hybridization was omitted.

Sample Preparation Method 4

One volume of a patient's unprocessed sputum was mixed with two volumes of IDF solution (Supra) in a tube and incubated at about 20-25° C. (ambient temperature) for 15 minutes. The sputum-IDF mixture is boiled for 15 minutes to release nucleic acids in solution and at the same time render the sample non-infectious. Nucleic acids can be purified by standard techniques from the boiled sample or the target nucleic acid of interest can be selected by sandwich hybridization using specific probes and magnetic beads as described by Shah et al. (Shah J. S., King W. Liu J., Smith J., Serpe G. and Popoff S., and. (1997). Assay improvements. U.S. Pat. No. 5,629,156.), which is incorporated herein by reference). The purified target can be amplified by PCR (for a DNA target) or RT-PCR (for an RNA target).

Probing of Samples

An oligonucleotide probe comprised of a DNA sequence that specifically hybridizes to the 23 S ribosomal RNA of *Mycobacterium tuberculosis* as described by Shah, Nietupski and Liu (U.S. Pat. No. 5,521,300) are preferably used in the detection of the presence of *M. tuberculosis* in cells. Examples of a suitable probe complex are:

P1. TB Probe

[SEQ ID NO: 1]
5'-Rhodamin Green-AGA-ACA-CGC-CAC-TAT-TCA-CAC-GCG-CGT-ATG-C-3' 66.5c P2-Tb-1 51-2c

[SEQ ID NO: 2]
5'-Rhodamin Green-TTC-GAG-GTT-AGA-TGC-CC-3'

P3. Mycobacterium Probe

[SEQ ID NO: 3]
5'-Tamra-ATC GCC CGC ACG CTC ACA GTT AAG CCG TGA GAT TTC-3' 68.7c P4 -Mycobacterium genus -54.1 c

[SEQ ID NO: 4]
5'-Tamra-GCA-TTA-CCC-GCT-GGC-3'

P5 -Burkholderia Probe

[SEQ ID NO: 5]
5'-FAM-CTT-GGC-TCT-AAT-ACA-GTC-GG-3' tm52c

PNA Probe.

In one embodiment, this probe complex was contacted to the nucleic acids of the fixed/pretreated sample in a hybridization buffer of 2.5 M GuSCN, 50 mM Tris (pH 7.8), 20 mM EDTA and 1% NP40 at 37° C. In an alternate embodiment, this probe complex was contacted to the nucleic acids of the fixed sample in a hybridization buffer of 50% formamide, 2×SSC (pH 7.4), 20 mM EDTA, 1% NP40 at 42° C.

Examples of a suitable oligonucleotide sequences for use in alternate probe complexes for the detection of *Mycobacteria* species are:

P2-Tb-1 51-2c

[SEQ ID NO: 2]
5'-Rhodamin Green-TTC-GAG-GTT-AGA-TGC-CC-3'

P3. Mycobacterium Probe

[SEQ ID NO: 3]
5'-Tamra-ATC GCC CGC ACG CTC ACA GTT AAG CCG TGA GAT TTC-3' 68.7c P4 -Mycobacterium genus -54.1 c

[SEQ ID NO: 4]
5'-Tamra-GCA-TTA-CCC-GCT-GGC-3'

SEQ ID NOs: 3 and 4 and the complements thereof are suitable for detection of *Mycobacteria* sp. SEQ ID NOs: 1 and 2 and the complements thereof, are suitable for detection of *M. tuberculosis*. SEQ ID NO: 5 is suitable for the detection of *Burkholderia* sp.

The ribosomal RNA sequence is chosen for use in the detection of the *Mycobacteria* pathogens because of the high abundance of rRNA in bacterial cells (1,000-10,000 copies). Preferably the oligonucleotide of the probe complex is a DNA with a sequence complimentary to *M. tuberculosis* rRNA. The oligonucleotide is preferably labeled at the 3' and 5' end with fluorescein. It will be recognized that a RNA oligonucleotide probe can be used as well.

As discussed above, the quantity of the total probe is a predetermined amount that should exceed the estimated amount of the available rRNA believed to be within the sample (about 100:1) in order to drive the hybridization reaction efficiently and to promote a high rate of probe:target annealing. In quantitative terms, this requires that a probe comprised of a 30-nucleotide long oligonucleotide be used in concentrations ranging from 1-10 µg/ml to produce reliable signal above background.

It should be appreciated that use of GuSCN also allows hybridization to be carried out at a much lower temperature than standard hybridization protocols. Hybridization of the specified probe specifically to the target (and not to host cells) in aqueous hybridization fluid such as sodium chloride would require a temperature of about 60-65° C. However, hybridization performed in the GuSCN or GuHCl hybridization buffer above, at about 37° C. ensures specificity.

One of the advantages of the in situ hybridization method is that relatively small numbers of cells comprise a sample and large numbers of identical samples may be processed over a short period of time. The unique in situ hybridization method described is extremely simple. The methods of the present invention can also be applied to any kind of sample, including, without limitation, paraffin-embedded tissue sections, acetone fixed samples.

The results of these experiments show the detection of the target (pathogen DNA) in the tested samples and no detection of the target in control samples. Detection of the target is consistently better in the samples treated with the IDF solutions of the present invention. One skilled in the art will appreciate, understand and know the IDF solutions of the present invention may be used in any situation requiring the effective entry of a probe (or other similar object) into a cell, pathogen (e.g., located in a cell) or organelle without undue experimentation.

It should be evident from the forging that the present invention provides compositions and methods for increasing the permeability of cells, cell walls, cell membranes, organelles and organelle membranes to aid, for example, in the detection of cellular components and/or pathogens.

What is claimed is:

1. A composition for increasing the permeability of cell walls and cell membranes of *Mycobacterium* sp., said composition comprising:
GuSCN (guanidine thiocyanate) at a concentration of approximately 2.0 to 3.3 M,
Tris-HCL at a concentration of approximately 10.0 to 100.0 mM and at a pH of approximately 7.0 to 9.0,
EDTA at a concentration of approximately 5 to 50 mM,
IGEPAL (octylphenoxy poly(ethyleneoxy)ethanol) at a concentration of approximately 0.1 to 2.0 percent (v/v),
acetic acid at a concentration of approximately 1.0 to 10 percent (v/v),
methanol at a concentration of approximately 20 to 50 percent (v/v), sodium cholate at a concentration of approximately 0.02 to 2.5 percent (w/v) and, sodium deoxycholate at a concentration of approximately 0.02 to 2.5 percent (w/v), whererin said composition is effective in permeabilizing the cell walls and cell membranes of *Mycobacterium* sp. but not effective in lysing *Mycobacterium* sp.

2. A method for detecting a target in a cell, comprising:
a) Contacting the cell with the composition of claim 1 to create a permeabilized cell;
b) Contacting the permeabilized cell of step (a) with a binding agent specific for binding to said target, and;
c) Detecting said binding agent of step (b).

3. The method of claim 2, wherein said target is selected from a group consisting of nucleic acids, peptides, glycoproteins, lipids, lipoproteins, viruses and prions.

4. The method of claim 2, wherein said binding agent is selected from a group consisting of nucleic acids, peptide nucleic acids, peptides, lipoproteins, glycoproteins and lipids.

5. The method of claim 2, wherein said binding agent additionally comprises a detection moiety.

6. The method of claim 5, wherein the detection moiety is selected from a group consisting of fluorescent markers, radioactive markers, dyes, colloidal metals, biotin/avidin and horseradish peroxidase.

7. The method of claim 2, wherein said detection is via a labeled antibody with affinity for said binding agent.

8. The method of claim 2, wherein said target is a nucleic acid from the microorganism *Mycobacterium tuberculosis*.

9. The method of claim 2, wherein said binding agent is an oligonucleotide complementary to a nucleic acid of the microorganism from *Mycobacterium tuberculosis*.

10. The method of claim 2, wherein said method additionally comprises background staining.

11. The method of claim 2, wherein said binding agent is an oligonucleotide complementary to a nucleic acid of the microorganism from *Mycobacterium* sp.

12. The method of claim 2, wherein said binding agent is an oligonucleotide complementary to a nucleic acid of fungi.

* * * * *